United States Patent [19]

White et al.

[11] Patent Number: 4,774,945
[45] Date of Patent: Oct. 4, 1988

[54] SPEECH FACILITATOR TUBE AND VALVE

[75] Inventors: Kenneth S. White, Wilmington, N.C.; George G. Siposs, Costa Mesa, Calif.

[73] Assignee: American Omni Medical, Costa Mesa, Calif.

[21] Appl. No.: 53,845

[22] Filed: May 26, 1987

[51] Int. Cl.⁴ .................................. A61M 15/08
[52] U.S. Cl. ..................... 128/207.18; 128/207.15; 128/207.16; 623/9
[58] Field of Search ............ 128/207.15, 207.16, 128/207.18; 623/9

[56] References Cited

U.S. PATENT DOCUMENTS

| | | | |
|---|---|---|---|
| 4,280,492 | 7/1981 | Latham | 128/207.16 |
| 4,449,523 | 5/1984 | Szachawicz et al. | 128/207.15 |
| 4,459,984 | 7/1984 | Liegher | 128/207.15 |
| 4,573,460 | 3/1986 | Szachawicz et al. | 128/207.15 |
| 4,593,689 | 6/1986 | White | 128/207.15 |
| 4,612,664 | 9/1986 | Walsh et al. | 623/9 |
| 4,633,864 | 1/1987 | Walsh | 128/207.15 |

Primary Examiner—A. Michael Chambers
Attorney, Agent, or Firm—Allen A. Dicke, Jr.

[57] ABSTRACT

Into patients intubated with an endotracheal tube for patient ventilation, a sound tube is inserted into the hypopharynx. A valve between the endotracheal tube and the ventilator can be manually actuated so that the patient's exhaled breath passes through a buzzer in the sound tube. The sound emanates from a location just above the natural vocal chords and can be articulated into intelligible speech by lips and tongue.

24 Claims, 3 Drawing Sheets

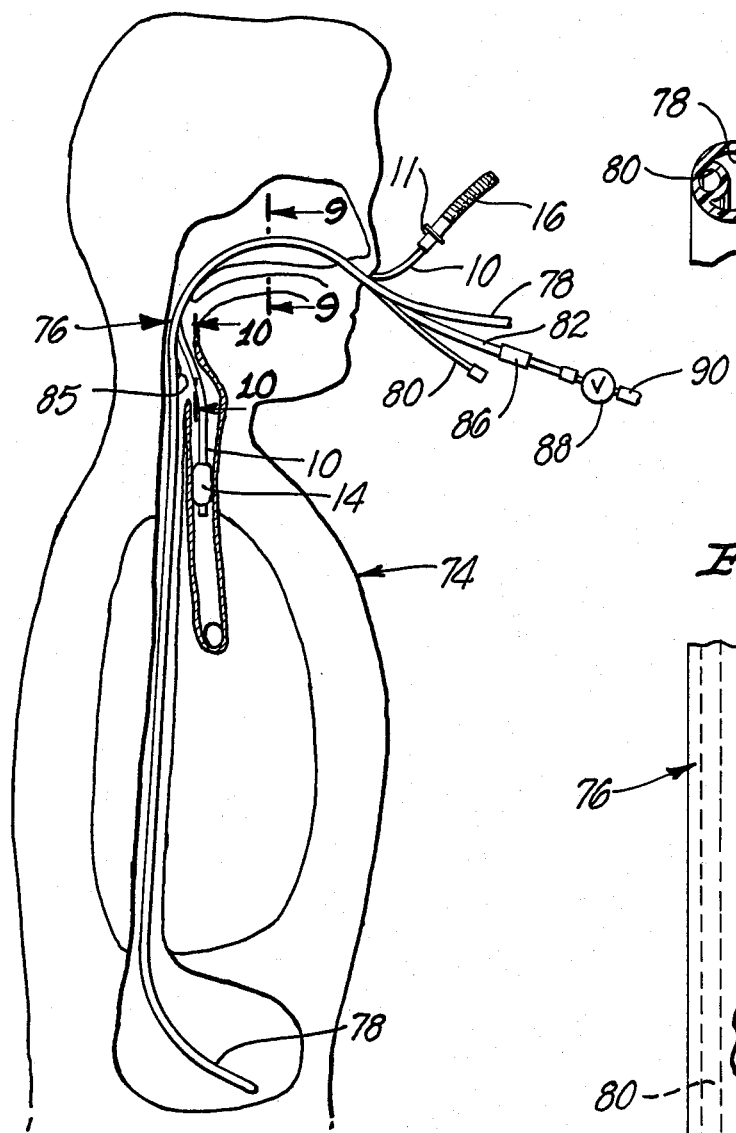
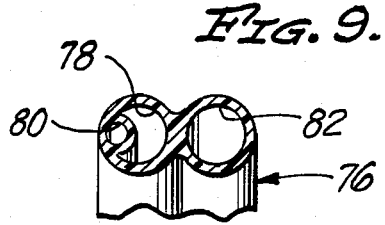
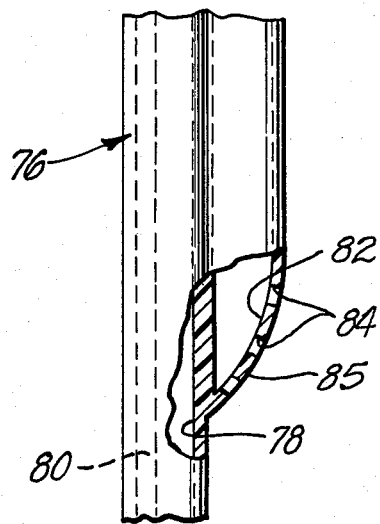

SPEECH FACILITATOR TUBE AND VALVE

FIELD OF THE INVENTION

This invention is directed to a sound tube carrying a buzzer with the outlet of the tube positioned at the hypopharynx so that the patient can articulate the sound of the buzzer into intelligible words by normal movement of the tongue and lips.

BACKGROUND OF THE INVENTION

Some post-operative patients have an endotracheal tube inserted through the nasal passage and terminating in the trachea. A ventilator is connected to the endotracheal tube and is utilized to control the patient's breathing. The ventilator inflates and deflates the patient's lung. The endotracheal tube passes through the vocal chords and thus makes them inoperative. Such patients cannot communicate by voice. The inability to communicate causes anxiety for many patients as well as frustration for the medical team and the patient's relatives.

When an endotracheal tube is in one nostril and a nasogastric tube is in the other nostril, the patient cannot communicate by voice. Since both nostrils are employed, there is no opportunity to pass a voice tube down into the hypopharynx. In other cases, the larynx or vocal chords are distorted or removed so that the patient has a permanent impairment of vocal capability. In each case, it is desirable to provide the patient with a device which permits him to articulate intelligible speech.

SUMMARY OF THE INVENTION

In order to aid in the understanding of this invention, it can be stated in essentially summary form that it is directed to a speech facilitator tube and valve, with the tube configured for placement through the nasal passages to terminate above the larynx. A buzzer is provided in the tube, and the tube has a gas supply to actuate the buzzer so that sound is produced which can be articulated into intelligible speech by action of the lips and tongue. When the tube is employed with an endotracheal tube for patient ventilation, a valve is provided to permit exhaled air to actuate the buzzer and the speech facilitator tube. When the tube is employed with a nasogastric tube, it can be attached thereto to the hypopharynx.

It is thus an object and advantage of this invention to provide a speech facilitator tube which contains a buzzer and is configured so that the tube can be installed with its lower end in the hypopharynx, just above the region of the larynx, so the buzzer in the tube delivers sound near the larynx from which the sound can be articulated into intelligible speech.

It is another object and advantage of this invention to provide a speech facilitator tube which is particularly useful in connection with endotracheal intubation of a patient, including a valve which causes exhaled ventilation air to be passed through the speech facilitator tube to actuate a buzzer therein and deliver sound to the hypopharynx.

It is another object and advantage of this invention to provide a speech facilitator tube and valve which is inexpensive so that it can be supplied in presterilized condition and disposed after use and provide a speech facilitator tube which is reliable and effective to produce intelligible speech.

Other purposes and advantages of this invention will become apparent from a study of the following portion of the specification, the claims and the attached drawings.

BRIEF DESCRIPTION OF THE DRAWINGS

FIG. 8 is a side-elevational view of a patient with nasogastric intubation incorporating the speech facilitator tube of this invention.

FIG. 9 is an enlarged section through the tube assembly, as seen generally along the line 9—9 of FIG. 8.

FIG. 10 is an enlarged view as seen generally along the line 10—10 of FIG. 8, with parts broken away and parts taken in section.

DESCRIPTION OF THE PREFERRED EMBODIMENTS

Figure 1:
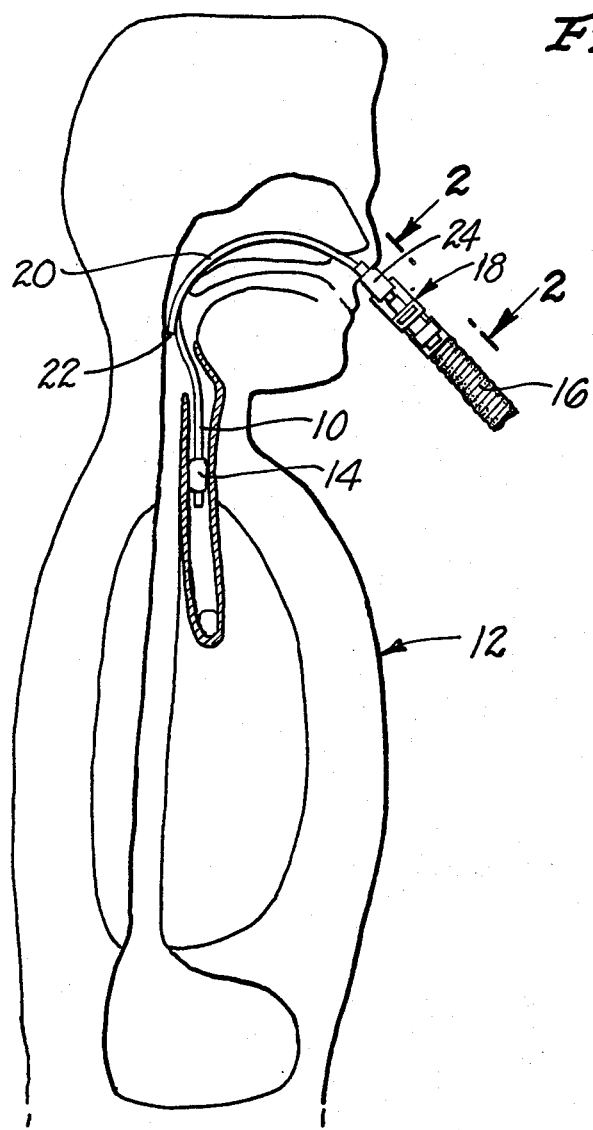
FIG. 1 is a side-elevational view of a patient with an endotracheal intubation, with parts broken away and parts taken in section to show the first preferred embodiment of the speech facilitator tube and valve of this invention.

Endotracheal tube is placed within the trachea of a patient to assist in breathing. Endotracheal tube 10 is shown in FIG. 1 to be nasally inserted in patient 12 into the trachea, below the larynx. Cuff 14 is attached to the end of tube 10 and is inflated to seal endotracheal tube with respect to the patient's trachea. A ventilator is connected to ventilator tube 16, which is connected through valve 18 to endotracheal tube 10. In the normal position of valve 18, ventilator tube 16 is directly connected to endotracheal tube 10 to provide normal ventilation. Normal ventilation comprises cyclically delivering air or oxygen-enriched air under gentle pressure and predetermined cycle volume through the ventilator tube and endotracheal tube to inflate the patient's lungs. At the end of each cycle, the ventilator removes the air or the lungs are permitted to normally contract and expel the air delivered on the previous cycle. In the normal position of valve 18, shown in FIGS. 2, 3, 4, 5 and 6, the expelled air goes back to the ventilator and is vented to atmosphere.

While the endotracheal tube is in place, all of the air delivered by the ventilator and the exhaled air passes through the endotracheal tube. Therefore, no air passes the vocal chords of the patient while he is intubated, and the tube incapacitates the chords; thus the patient cannot speak. Voice tube 20 is nasally inserted and extends into the hypopharynx just above the larynx of the patient, as indicated in FIG. 1. Tube 20 is open at its distal end 22. Voice tube 20 carries an air-operable reed or buzzer therein. The buzzer 24 is located at the valve, as seen in FIG. 1, but alternatively the buzzer could be positioned within the length of the tube or at the distal end. Regardless of where the buzzer is located, the sound emanates at the open end 22 of the tube 20, which is close to the normal location of the vocal chords. The buzzer sound can be articulated into intelligible words by normal movement of the tongue and lips. If the buzzer is located at the proximal connection end of the voice tube, the sound is carried through the tube and the sound is delivered into the hypopharynx just below the uvula and just above the vocal chords, at the distal end of the voice tube. Whether the sound is generated at the distal end or delivered there, it can be articulated into intelligible words by normal movement of the tongue and lips, as previous described.

Figure 2:
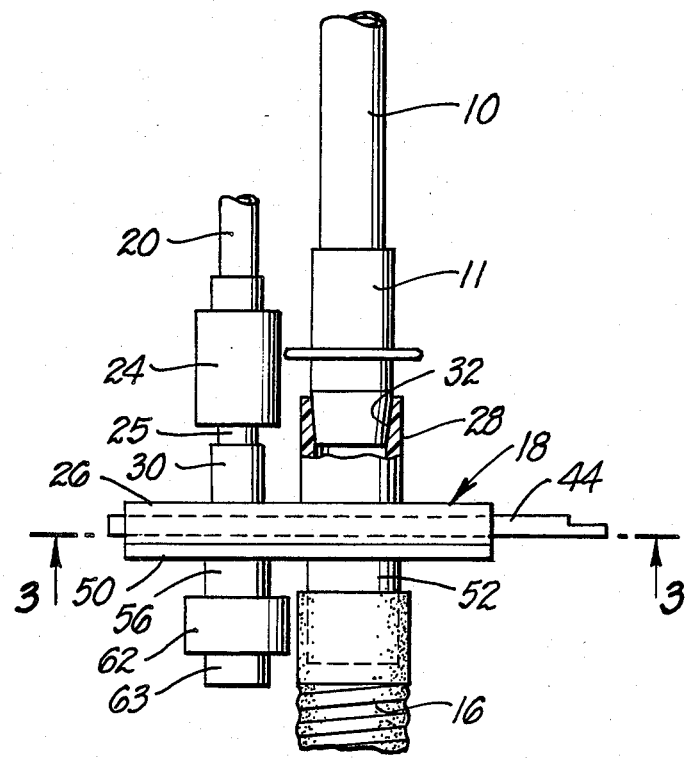
FIG. 2 is an enlarged plan view of the valve, as seen along the line 2—2 of FIG. 1.

In order to make the buzzing sound, gas must be delivered through voice tube 20 to a sufficient extent to actuate the buzzer 24. The delivery can simply be by connection to a pressurized source, such as compressed air or oxygen, or, since the patient is used to speaking as he is exhaling, it is preferable to employ the breath delivered by the contracting lungs to energize the buzzer. This is accomplished by means of valve 18. Valve 18 has a body 26 on which are secured endotracheal tube boss 28 and voice tube boss 30. These bosses are tubular and are sized to connect the respective tubes. Fitting 11 is secured on the end of tube 10 and forms a standard part thereof. Fitting 11 has a tapered nose and engages securely within the tapered opening 32 in endotracheal tube boss 28. Voice tube boss 30 has a central opening 34. Buzzer 24 has a nose 25 which inserts into and seals with respect to the opening 34 in boss 30. Voice tube 20 is received in a tube fitting on the top of the buzzer, as seen in FIG. 2.

Each of the bosses is a valve port. Slot 36 is formed through the body along the length of the body. Slot 36 is a parallel slot, except for guide pins 38 and 40 formed as part of the body and extending into the slot, and spring stop 42 formed as part of the body and positioned at the left end of the slot, as seen in FIG. 3, where it extends partway across the slot.

Valve member 44 is of generally rectangular configuration to fit within the slot 36 and slide therein. Slots 46 and 48 respectively receive guide pins 38 and 40 to limit the longitudinal sliding of the valve member in the valve body. The pins also facilitate aligning and assembling the parts 50 and 26.

Figure 4:
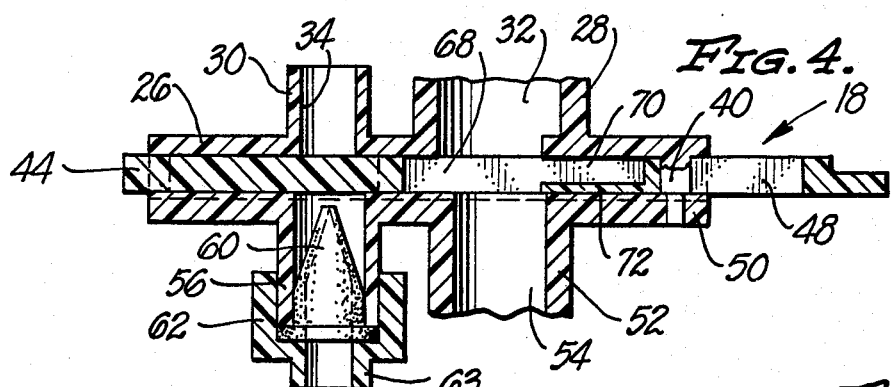
FIG. 4 is a section of the valve, as seen generally along the line 4—4 of FIG. 3.
Figure 5:
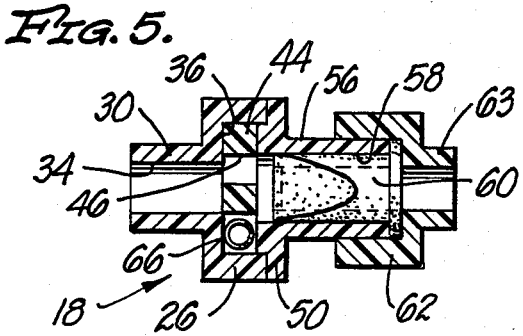
FIG. 5 is a transverse section through the valve, as seen generally along the line 5—5 of FIG. 3.
Figure 6:
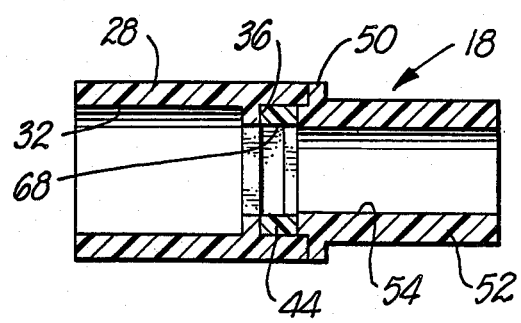
FIG. 6 is another transverse section through the valve, as seen generally along the line 6—6 of FIG. 3.

Valve cover 50 has openings which locate on pins 38 and 40, as seen with respect to pin 40 on the right side of FIG. 4. Valve cover 50 is also tee-shaped to enter a short distance into the slot 36 for proper alignment and security with respect to the body. The cover is permanently attached by welding or adhesive, but valve member 44 is allowed to slide freely. This tee-shape is seen in FIGS. 5 and 6. Cover 50 has ventilator boss 52 thereon for connection to ventilator tube 16. Opening 54 in boss 52 is in alignment with opening 32. Valve cover 50 also carries check valve boss 56 thereon, which has its opening 58 in alignment with opening 34 in voice tube boss 30. Resilient check valve 60 is positioned in check valve boss 56. The check valve 60 is in the form of a duckbill valve directed upward, from atmosphere toward the voice tube opening 34. Fitting 62 holds the resilient duckbill check valve 60 in place and has an opening therethrough and a hose nipple 63 thereon.

Figure 3:
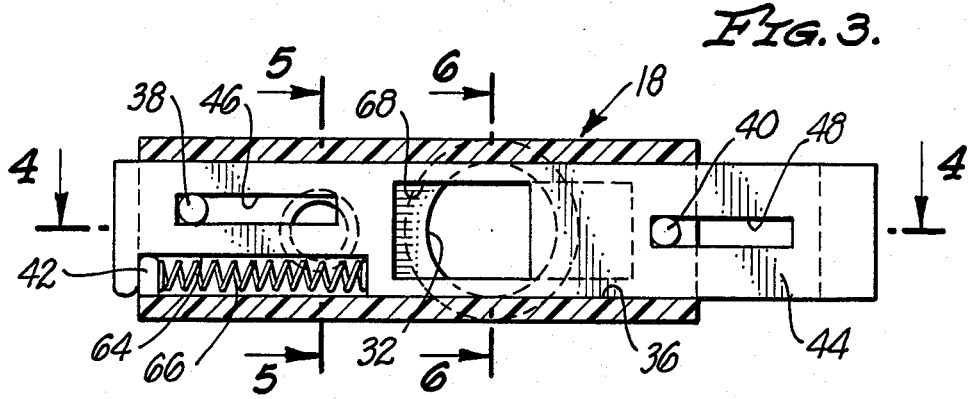
FIG. 3 is a further enlarged sectional view of the valve, as seen along the line 3—3 of FIG. 2, shown in the ventilating position.
Figure 7:
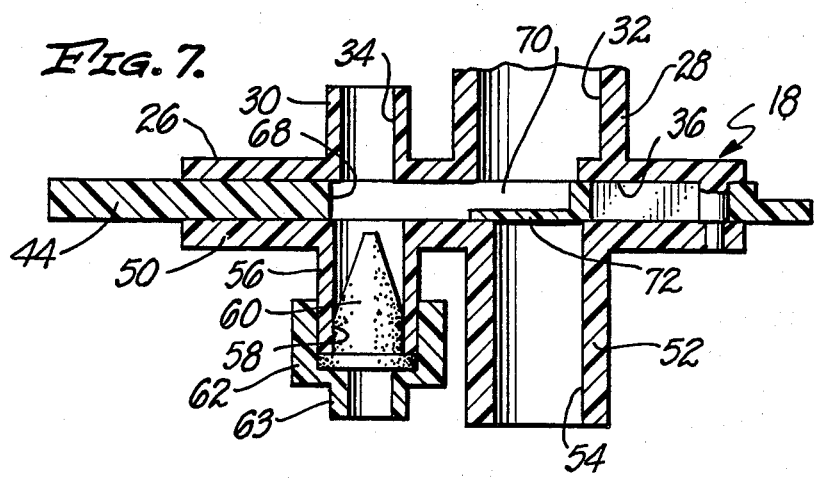
FIG. 7 is a longitudinal section through the valve, similar to the section shown in FIG. 4, showing the valve in the speaking position, using exhaled breath.

As seen in FIG. 3, spring pocket 64 contains compression spring 66 which resiliently urges valve member 44 to the rightmost position seen in FIG. 3. In this position, valve opening 68 is in alignment between ventilator opening 54 and endotracheal tube opening 32. In this position, there is continuity between the ventilator and the endotracheal tube for normal ventilation and allows no escape of air to voice tube through boss 30. Valve opening 68 has a recess 70 which is above gate 72 formed as part of the sliding valve member 44. When the sliding valve member 44 is moved to its leftmost stop position by finger pressure, against the urging of spring 66, the ventilator opening 54 is closed off, but endotracheal tube opening 32 is connected to voice tube opening 34 and valve 60, see FIG. 7. In this position, the exhaling patient breathes out through tube 10, through opening 32 and boss 28, through the recess 70 and valve opening 68 back into voice tube opening 34 and into the voice tube 20 itself. This exhalation energizes buzzer 24. The sound is in the area of the patient's larynx so that by normal movement of the tongue and lips, the patient can articulate the buzzing sound into intelligible words. The patient does this for one exhalation, and thereupon releases the sliding valve member so that the next lung inflation can be accomplished by the ventilator.

The ventilation system is often used on patients who have some breathing capability to create sufficient breathing volume on the correct breathing cycle. Such patients may try to inhale while the valve member 44 is in the speaking position illustrated in FIG. 7. With the valve member in that position, he cannot inhale air from the ventilator. In this circumstance, check valve 60 opens to permit entry of room air, to prevent the patient from feeling deprived of air. If the patient desires, he can hold the valve member 44 in the active position shown in FIG. 7, inhale through check valve 60, and exhale through voice tube 20 to provide the buzzing sound which he can articulate into words. The employment of the check valve 60 prevents situations in which the patient tries to inhale but cannot. When the patient releases the sliding valve member 44 from his fingers, the spring returns it to the normal position.

In those cases where the patient relies upon the ventilator for exhalation, he cannot use the sliding valve member 44 during exhalation to supply air through the voice tube. To supply the gas necessary to energize the buzzer in these circumstances, an oxygen or air line can be connected to connection nipple 63. A valve in such a line would control the delivery of air to the buzzer, and in turn, control the generation and delivery of sound at the distal end 22 of voice tube 20. The connection of a pressurized gas supply to the nipple 63 does not require the translation of sliding member 44 for actuation of the buzzer.

The speech facilitator tube and valve described with respect to FIGS. 1 through 7 permits the insertion of the voice tube through one nostril when the other is occupied by the endotracheal tube 10. Sometimes it is medically helpful or required to employ a nasogastric tube together with the endotracheal tube. Since both nostrils are occupied, a separate voice tube cannot be used. Patient 74, shown in FIG. 8, has a nasally inserted endotracheal tube 10 and also has a nasogastric tube 76 inserted through his nasal passages, through his hypopharynx, into his stomach. The nasogastric tube 76 has three lumens therein. Lumen 78 is a gastric lumen which passes into the stomach. At its upper end, it is connected to a suction source. Lavage or air bleed lumen 80 also passes into the stomach and is separately connected at its upper end to deliver lavage fluids to the stomach, as required or to permit air to enter the stomach. Voice tube lumen 82 terminates partway along the length of the nasogastric tube and has one or more ports 84 at its lower end 85. When the nasogastric tube is properly positioned, the ports 84 are in the hypopharynx. Buzzer 86 is positioned in voice tube 82. It may be at either end of the voice tube or along its length. In FIG. 10, it is illustrated as being adjacent the upper end of the voice tube, exterior to the patient. The voice tube and buzzer are supplied with gas under pressure. Alternatively, a valve 18 could be connected to the nasogastric tube 10, ventilator tube 16, and voice tube 82 so as to use the patient's exhaled breath. In the present case, valve 88 controls the flow of gas under pressure from pressure line 90. The pressure line 90 may be an humidified oxygen or a compressed air line, or other convenient source. Valve 88 can conveniently be a spring-loaded pushbutton valve, where the valve is normally closed and when pressed, it is opened. When the patient wants to speak, the valve 88 is opened so that gas under pressure is delivered to buzzer 86. The buzzer sounds, and the vibrations are delivered by means of the voice tube 82 to the hypopharynx. Once the vibrations are acoustically delivered in this area, the vibrations can be articulated into intelligible sounds by means of the mouth and tongue. In this way, a nasogastrically intubated patient can vocally communicate with those around him.

This invention has been described in its presently contemplated best modes, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A speech facilitator system for use with a patient having a hypopharynx comprising:
    a voice tube having proximal and distal ends, said voice tube being configured so that its distal end can be positioned in the hypopharynx of a patient and its proximal end can be positioned nasally exterior of the patient;
    a gas-actuated buzzer connected to said voice tube to produce audible buzzing when gas is delivered through said voice tube from its proximal to its distal end;
    a valve connected to said voice tube at its proximal end to control the delivery of gas under pressure through said voice tube and through said buzzer to result in a buzzing sound in the hypopharynx of the patient; and
    means on said valve for connection to a second tube which is for passing through the patient's nasal passages and extending through his hypopharynx and through the vocal chords which renders his vocal chords inoperative.

2. A speech facilitator system for use with a patient having a hypopharynx comprising:
    a voice tube having proximal and distal ends, said voice tube being configured so that its distal end can be positioned in the hypopharynx of a patient and its proximal end can be positioned nasally exterior of the patient;
    a gas-actuated buzzer connected to said voice tube to produce audible buzzing when gas is delivered through said voice tube from its proximal to its distal end;
    a valve connected to said voice tube at its proximal end to control the delivery of gas under pressure through said voice tube and through said buzzer to result in a buzzing sound in the hypopharynx of the patient; and
    a second tube connected to said valve body, said second tube being an endotracheal tube so that said valve can deliver air exhaled through said endotracheal tube to said voice tube.

3. The speech facilitator system of claim 2 wherein said valve has an unactuated position and an actuated position, said valve being positionable with respect to the patient so that a person can move said valve to its actuated position for connecting air exhaled through said endotracheal tube to said voice tube.

4. The speech facilitator system of claim 3 wherein said valve has means thereon for connection to said endotracheal tube and to said voice tube and said valve also has means thereon for connection to a ventilator, said valve being arranged so that when it is in its unactuated position, said ventilator connection is connected to said endotracheal tube connection.

5. The speech facilitator system of claim 4 wherein said valve is configured so that when it is in its unactuated position, said voice tube connection is out of communication with said ventilator connection and said endotracheal tube connection.

6. The speech facilitator system of claim 4 wherein said valve is configured so that in its actuated position, endotracheal tube connection is in communication with said voice tube connection and said ventilator connection is out of communication with said endotracheal tube connection.

7. The speech facilitator system of claim 6 wherein said valve includes a check valve, said check valve being connected between said endotracheal tube connection and the atmosphere and directed to permit inflow of air into said endotracheal tube connection when a suction is drawn thereon.

8. The speech facilitator system of claim 7 wherein said valve is configured so that when it is in its unactuated position, said voice tube connection is out of communication with said ventilator connection and said endotracheal tube connection.

9. The speech facilitator system of claim 2 wherein said valve has a body and has a sliding valve member in said body, said body having a connection boss for connection to said endotracheal tube and having a connection boss for connection to said voice tube, said valve member being slidable from an unactuated position wherein said endotracheal tube boss is out of communication with said voice tube boss to an actuated position wherein said endotracheal tube boss is in connection with said voice tube boss and a spring in said valve body to urge said sliding valve member from its actuated position toward its unactuated position.

10. The speech facilitator system of claim 9 wherein a portion of said valve member extends out of said body so that valve member can be manually engaged to move said valve member from its unactuated position to its actuated position.

11. A speech facilitator system for use with a patient having a hypopharynx comprising:
    a voice tube having proximal and distal ends, said voice tube being configured so that its distal end can be positioned in the hypopharynx of a patient and its proximal end can be positioned nasally exterior of the patient;

a gas-actuated buzzer connected to said voice tube to produce audible buzzing when gas is delivered through said voice tube from its proximal to its distal end;

a valve connected to said voice tube at its proximal end to control the delivery of gas under pressure through said voice tube and through said buzzer to result in a buzzing sound in the hypopharynx of the patient; and a nasogastric tube connected to said valve for positioning so that its proximal end is exterior of the nasal structure of the patient and its distal end is in the stomach of the patient, said voice tube and said nasogastric tube being separate tube passages in the same tube body.

12. The speech facilitator system of claim 11 wherein said voice tube passage has sound emitting ports in the hypopharynx of the patient when the distal end of the nasogastric tube is positioned in the stomach of the patient.

13. The speech facilitator system of claim 12 wherein said gas-operated buzzer is at said proximal end of said voice tube.

14. A speech facilitator system comprising:

a nasogastric tube having a proximal end and a distal end, said nasogastric tube being sufficiently long so that when its distal end is in the stomach of a patient, its proximal end is nasally exterior of the patient;

a voice tube attached to said nasogastric tube, said voice tube having a distal end and a proximal end with the distal ends of said nasogastric tube and said voice tube being positioned with respect to each other so that said distal end of said voice tube is in the hypopharynx of the patient when said distal end of said nasogastric tube is in the stomach of the patient;

a sound producing buzzer attached to said proximal end of said voice tube; and a valve connected to said buzzer to deliver gas under pressure to said buzzer when said valve is actuated to cause said buzzer to make sound which said voice tube delivers to the hypopharynx of the patient whereby the sound can be articulated into speech.

15. The speech facilitator system of claim 14 wherein said distal end of said voice tube is open to the hypopharynx by means of ports in said voice tube.

16. The speech facilitator system of claim 15 wherein said valve is a manually actuated valve.

17. The speech facilitator system of claim 14 wherein said voice tube is integrally formed with said nasogastric tube.

18. A speech facilitator system comprising:

a valve having a body, a valve member movable with respect to said body to cause valving changes within said body, said body having connection ports thereon for a voice tube, and an endotracheal tube and a ventilator tube;

a voice tube having a proximal and having a distal end, said proximal end being for interconnection to said voice tube port on said valve body;

a gas-operated buzzer in said voice tube so that when gas is delivered through said voice tube and said distal end of said voice tube is positioned in the hypopharynx of a patient, said voice tube delivers sound to the hypopharynx of the patient so that the patient can articulate intelligible words by normal movement of tongue and lips;

said valve member being movable from an unactuated to an actuated position and being configured so that when in its unactuated position, said ventilator connection port is in communication with said endotracheal tube connection port and when in said actuated position, said endotracheal tube port is in connection with said voice tube port and said ventilator connection port is out of communication therewith so that when in its actuated position, gas delivered to said endotracheal tube connection port is delivered to said voice tube for actuating said buzzer.

19. The speech facilitator system of claim 18 wherein there is a spring interengaged between said valve body and said valve member to urge said valve member toward its unactuated position.

20. The speech facilitator system of claim 19 wherein said valve member extends exteriorly of said body so that said valve member can be manually engaged to move said valve member from its unactuated position to its actuated position.

21. The speech facilitator system of claim 20 wherein said valve member is a slidable valve member sliding in a slot in said valve body.

22. The speech facilitator system of claim 18 wherein said body carries a check valve boss thereon together with a check valve within said check valve boss, said check valve being out of communication with said endotracheal tube connection port when said valve is in its unactuated position and in communication with said endotracheal tube connection port when said valve member is in its actuated position.

23. The speech facilitator system of claim 22 wherein said check valve is a duckbill valve inserted within said check valve boss.

24. The speech facilitator system of claim 23 wherein said check valve boss is substantially opposite said voice tube connection port on said body so that both said check valve port and said voice tube connection port are in communication with said endotracheal tube connection port at the same time.

* * * * *